United States Patent
Kim et al.

(10) Patent No.: US 10,059,917 B2
(45) Date of Patent: Aug. 28, 2018

(54) APPARATUS AND METHOD OF STIMULATING CELLS USING 3D CLINOSTAT AND ULTRASONIC WAVE

(71) Applicant: Yonsei University Wonju Industry-Academic Cooperation Foundation, Wonju-si, Gangwon-do (KR)

(72) Inventors: Han Sung Kim, Wonju-si (KR); Ji Hyung Park, Wonju-si (KR); Jong Bum Seo, Wonju-si (KR); Sinae Eom, Seoul (KR); Jung Woo Son, Seoul (KR); Tae Min Shin, Wonju-si (KR); Dong Hyun Seo, Wonju-si (KR); Dong Hyun Hwang, Seongnam-si (KR); Seong Guk Kim, Wonju-si (KR)

(73) Assignee: YONSEI UNIVERSITY WONJU INDUSTRY-ACADEMIC COOPERATION FOUNDATION, Gangwon-do (KR)

( * ) Notice: Subject to any disclaimer, the term of this patent is extended or adjusted under 35 U.S.C. 154(b) by 237 days.

(21) Appl. No.: 14/892,520

(22) PCT Filed: Feb. 13, 2014

(86) PCT No.: PCT/KR2014/001189
§ 371 (c)(1),
(2) Date: Nov. 19, 2015

(87) PCT Pub. No.: WO2014/189196
PCT Pub. Date: Nov. 27, 2014

(65) Prior Publication Data
US 2016/0115437 A1    Apr. 28, 2016

(30) Foreign Application Priority Data

May 21, 2013 (KR) ......................... 10-2013-0057086

(51) Int. Cl.
*C12M 1/42* (2006.01)
*C12M 1/34* (2006.01)
(Continued)

(52) U.S. Cl.
CPC .............. *C12M 35/04* (2013.01); *C12M 1/34* (2013.01); *C12M 3/00* (2013.01); *C12M 25/06* (2013.01); *C12M 23/12* (2013.01); *C12M 27/16* (2013.01)

(58) Field of Classification Search
CPC ....... C12M 23/12; C12M 27/16; C12M 35/04
See application file for complete search history.

(56) References Cited

U.S. PATENT DOCUMENTS

| | | |
|---|---|---|
| 2005/0028650 A1 | 2/2005 | Tassano et al. |
| 2012/0115224 A1 | 5/2012 | Ochiai et al. |
| 2013/0022957 A1* | 1/2013 | Chen ...................... C12N 13/00 435/3 |

FOREIGN PATENT DOCUMENTS

| | | |
|---|---|---|
| JP | 2007-178356 A | 7/2007 |
| WO | 2007-076865 A1 | 7/2007 |
| WO | 2010-003207 A1 | 1/2010 |

* cited by examiner

*Primary Examiner* — William H. Beisner
(74) *Attorney, Agent, or Firm* — Novick, Kim & Lee, PLLC; Jae Youn Kim

(57) ABSTRACT

Provided is an apparatus for stimulating cells using a 3D clinostat and ultrasonic waves in experiment equipment for studying adverse influences on a human body under microgravity and taking a countermeasure against the influences. Further, provided is a method of stimulating cells using a 3D clinostat and ultrasonic waves to study adverse influences on a human body under microgravity and to take a countermeasure against the influences.

8 Claims, 4 Drawing Sheets

(51) Int. Cl.
  *C12M 3/00* (2006.01)
  *C12M 1/12* (2006.01)
  *C12M 1/32* (2006.01)
  *C12M 3/06* (2006.01)

APPARATUS AND METHOD OF STIMULATING CELLS USING 3D CLINOSTAT AND ULTRASONIC WAVE

TECHNICAL FIELD

The present invention relates to an apparatus and a method of stimulating cells using a 3D clinostat and ultrasonic waves, particularly, to an apparatus and a method of stimulating cells using ultrasonic waves to take a countermeasure against adverse influence on the cells under microgravity.

BACKGROUND ART

Recently, people have a considerable interest in manned space flight projects and space life science relating to the projects.

A human mission to Mars takes about two and a half years to return to earth, and when a human body is exposed to the space environment for a long period of time, the biological tissues are considerably changed, which may influence missions in the space. For example, the bone, one of the important tissues of a human body, decreases in bone mineral density by about 1% a month, so it may cause a severe problem when a human stays in space for a long period of time.

Accordingly, it is required to take a counterpart that can minimize adverse influences on a human body under microgravity in a space environment in order to successfully proceed with space projects.

Many studies using a 3D-clinostat, for example in US Patent Application Publication No. 2005-028650 A1, have been made to study influences under a space environment, but there is little experiment apparatus capable of performing a study about a countermeasure against adverse influences under the space environment, that is, microgravity. In those apparatuses, there is no apparatus capable of estimating a loss in musculoskeletal system of a human body and taking a countermeasure against the loss.

SUMMARY OF INVENTION

Technical Problem

The present invention has been made in an effort to solve the problems and an object of the present invention is to provide an apparatus including an ultrasonic wave output unit on a 3D clinostat to study a countermeasure against adverse influences on a human body under microgravity, and a method using the apparatus.

Solution to Problem

According to an aspect of the present invention, there is provided an apparatus for stimulating cells using a 3D clinostat and ultrasonic waves in experiment equipment for studying adverse influences on a human body under microgravity and taking a countermeasure against the influences. The apparatus includes: a base plate; supports each having a first end coupled to a side on the top of the base plate; an outer frame formed by four members coupled in a rectangle and rotating about an axis between the two supports spaced at a predetermined distance from each other; an inner frame formed by four members coupled in a rectangle, disposed inside the outer frame, and rotating about an axis perpendicular to the rotational direction of the outer frame; a cultivating plate fixed inside the inner frame to cultivate cells; a first motor unit disposed on the base plate or one of the supports and connected to the outer frame to transmit torque; a second motor unit disposed on the outer side of the outer frame and connected to the inner frame to transmit torque; a controller electrically connected to the first motor unit and the second motor unit to control the first motor unit and the second motor unit; an output unit fixing member, such as an ultrasonic fixing member, fixed to the inner frame at a predetermined distance from the top of the cultivating plate and having a longitudinally oblong fixing hole; an ultrasonic wave output unit, such as an ultrasonicator, disposed at a side in the oblong fixing hole of the output unit fixing member; and an ultrasonic device connected to the ultrasonic wave output unit and stimulating cells on the cultivating plate.

According to another aspect of the present invention, there is provided a method of stimulating cells using a 3D clinostat and ultrasonic waves to study adverse influences on a human body under microgravity and to take a countermeasure against the influences. The method includes: (a) installing a 3D clinostat, which includes: a base plate; supports each having a first end coupled to a side on the top of the base plate; an outer frame formed by four members coupled in a rectangle and rotating about an axis between the two supports spaced at a predetermined distance from each other; an inner frame formed by four members coupled in a rectangle, disposed inside the outer frame, and rotating about an axis perpendicular to the rotational direction of the outer frame; a first motor unit disposed on the base plate or one of the supports and connected to the outer frame to transmit torque; a second motor unit disposed on the outer side of the outer frame and connected to the inner frame to transmit torque, into a laboratory; (b) fixing a cultivating plate for cultivating cells inside the inner frame; (c) disposing an output unit fixing member, such as an ultrasonicator fixing member, having a longitudinal oblong fixing hole with an ultrasonic wave output unit, such as an ultrasonicator, fixed therein, at a predetermined distance from the top of the cultivating plate; (d) connecting a controller to the first motor unit and the second motor unit; (e) connecting the ultrasonic wave output unit and an ultrasonic device; and (f) stimulating cells on the cultivating plate by operating the controller and the ultrasonic device.

Advantageous Effect(s) of Invention

According to the present invention, it is possible to study an adverse influence on a human body under microgravity and to study a countermeasure against the influence.

That is, it is possible to study both of an adverse influence on a human body and a countermeasure against the influence in space life by making an environment similar to the space environment, even without going out into space.

DESCRIPTION OF EMBODIMENTS

Hereinafter, an apparatus and a method of stimulating cells using a 3D clinostat and ultrasonic waves according to the present invention will be described in detail with reference to the accompanying drawings.

Figure 1:
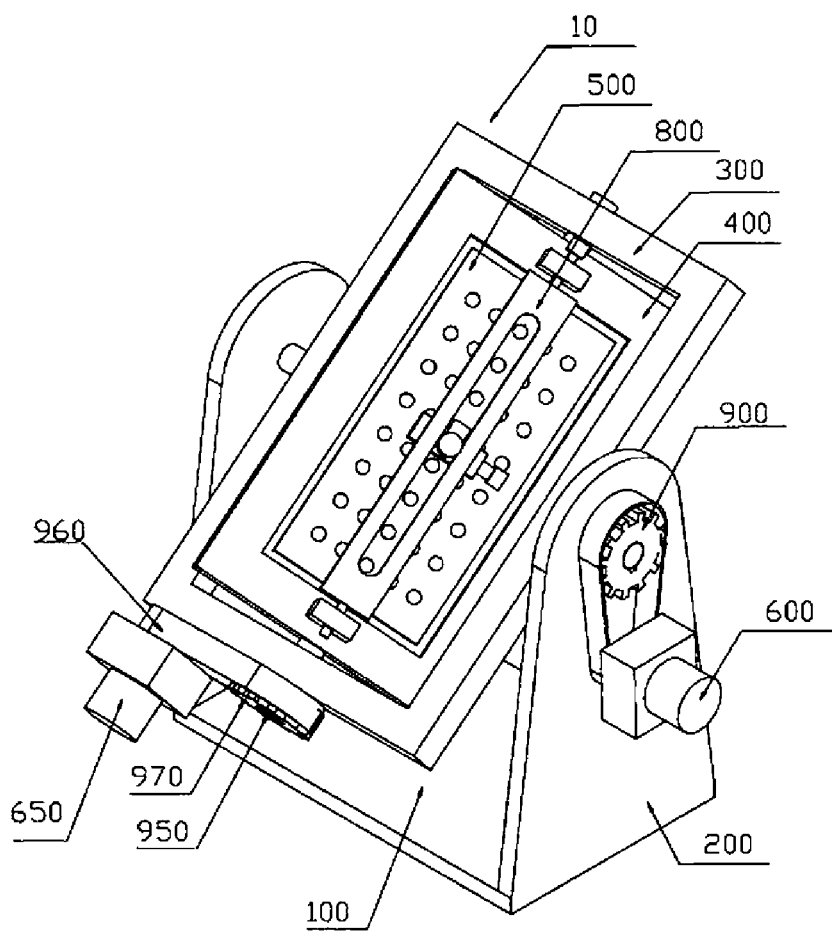
FIG. 1 is a perspective view showing an apparatus for stimulating cells of the present invention.
Figure 2:
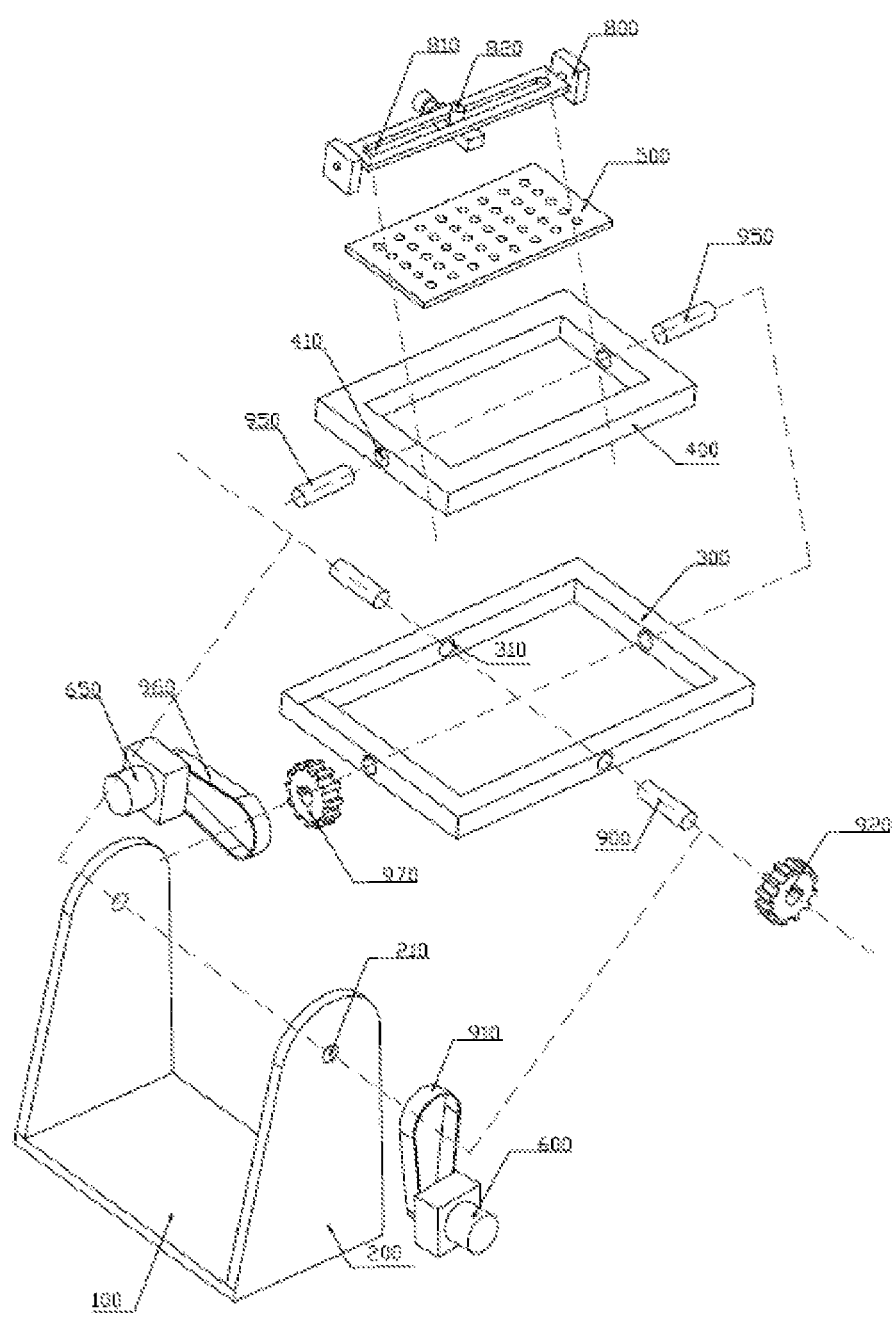
FIG. 2 is an exploded perspective view of FIG. 1.

FIG. 1 is a perspective view showing an apparatus for stimulating cells of the present invention and FIG. 2 is an exploded perspective view of FIG. 1.

Figure 3:
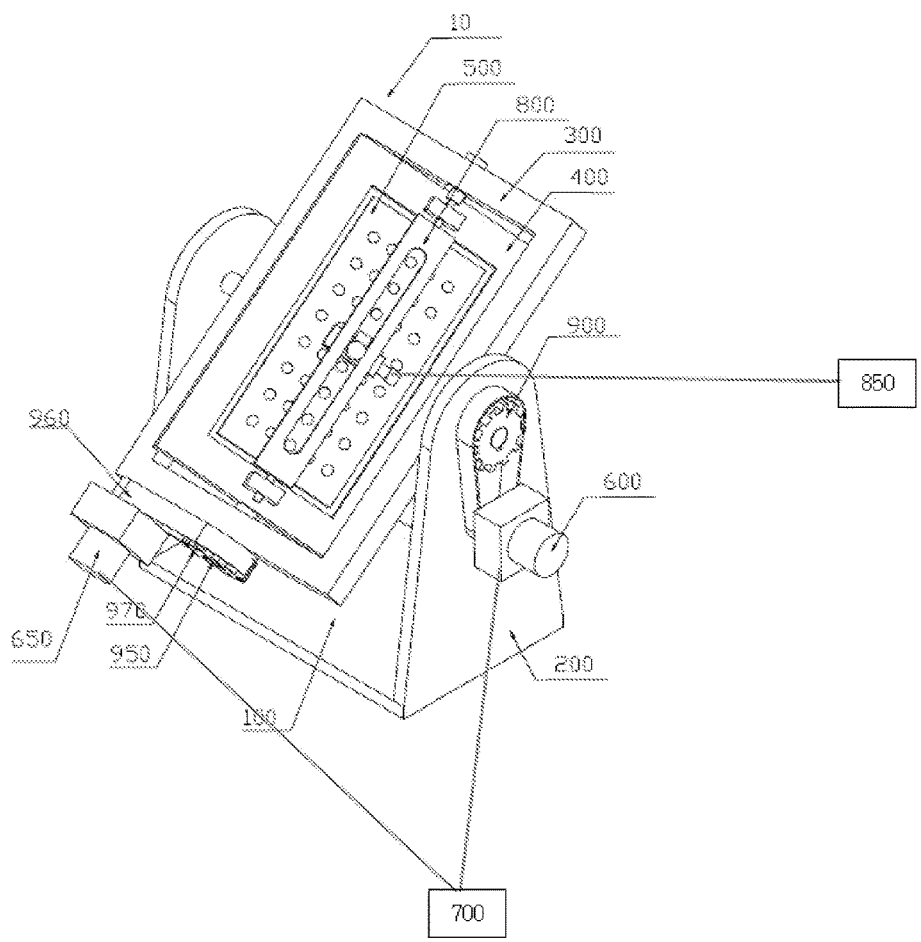
FIG. 3 is a perspective view showing a controller and an ultrasonic device connected to each other in FIG. 1.
Figure 4:
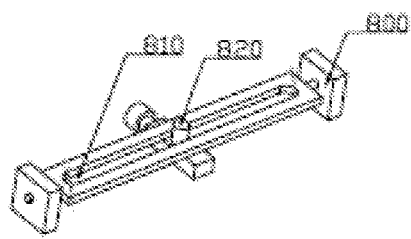
FIG. 4 is a perspective view showing an ultrasonic wave output unit coupled to an output unit fixing member.

FIG. 3 is a perspective view showing a controller and an ultrasonic device connected to each other in FIG. 1. FIG. 4 is a perspective view showing an ultrasonic wave output unit coupled to an output unit fixing member.

The present invention provides an apparatus 10 for stimulating cells using a 3D clinostat and ultrasonic waves, particularly, in experiment equipment for studying adverse influences on a human body under microgravity and taking a countermeasure against the influences. The apparatus 10 includes: a base plate 100; supports 200 each having a first end coupled to a side on the top of the base plate 100; an outer frame 300 formed by four members coupled in a rectangle and rotating about an axis between the two supports 200 spaced at a predetermined distance from each other; an inner frame 400 formed by four members coupled in a rectangle, disposed inside the outer frame 300, and rotating about an axis perpendicular to the rotational direction of the outer frame 300; a cultivating plate 500 fixed inside the inner frame 400 to cultivate cells; a first motor unit 600 disposed on the base plate 100 or one of the supports 200 and connected to the outer frame 300 to transmit torque; a second motor unit 650 disposed on the outer side of the outer frame 300 and connected to the inner frame 400 to transmit torque; a controller 700 electrically connected to the first motor unit 600 and the second motor unit 650 to control the first motor unit 600 and the second motor unit 650; an output unit fixing member 800 fixed to the inner frame 400 at a predetermined distance from the top of the cultivating plate 500 and having a longitudinally oblong fixing hole 810; an ultrasonic wave output unit 820 disposed at a side in the oblong fixing hole 810 of the output unit fixing member 800; and an ultrasonic device 850 connected to the ultrasonic wave output unit 820 and stimulating cells on the cultivating plate 500.

The present invention relates to an apparatus 10 for stimulating cells that includes the base plate 100, the supports 200, the outer frame 300, the inner frame 400, the cultivating plate 500, the first motor unit 600, the second motor unit 650, the controller 700, the output unit fixing member 800, the ultrasonic wave output unit 820, and the ultrasonic device 850.

Recently, people have a considerable interest in manned space flight projects and space life science relating to the projects. A human mission to Mars takes about two and a half years to return to earth, and when a human body is exposed to the space environment for a long period of time, the biological tissues are considerably changed, which may influence missions in the space. For example, the bone, one of the important tissues of a human body, decreases in bone mineral density by about 1% a month, so it may cause a severe problem when a human stays in space for a long period of time.

Accordingly, it is required to take a counterpart that can minimize adverse influences on a human body under microgravity in a space environment in order to successfully proceed with space projects.

Many studies using a 3D-clinostat, for example in US Patent Application Publication No. 2005-028650 A1, have been made to study influences under a space environment, but there is no experiment apparatus capable of performing a study about a countermeasure against adverse influences under the space environment, that is, microgravity. In those apparatuses, there is no apparatus capable of estimating a loss in musculoskeletal system of a human body and taking a countermeasure against the loss.

To solve the problem, in this invention, an apparatus that stimulates cells cultivated under microgravity using the ultrasonic device 850 in order to observe influences on cells under microgravity has been developed. That is, the present invention allows for studying a method capable of removing adverse influences that may be applied to a human body in a space environment.

The base plate 100 is a necessary plate on which the apparatus 10 for stimulating cells of the present invention is set. In general, the base plate may be made of any materials as long as it is a flat plate for setting the apparatus 10 for stimulating cells, and when the apparatus of the present invention is set on a specific structure or in a specific box, the base plate means the structure or the bottom of the box.

The supports 200 are members for supporting the outer frame 300, which will be described below, and each have an end coupled to a side on the top of the base plate 100. A first rotational hole 210 is formed at second ends of the supports 200 to be easily coupled to the outer frame 300. The supports 200 are common plates for supporting frames and any materials are available as long as they satisfy necessary strength.

The outer frame 300 disposed rotatably about an axis between the two supports 200 formed by four members coupled in a rectangle and spaced at a predetermined distance from each other. A second rotational hole 310 is formed through each member of the outer frame 300 for easy coupling. That is, the outer frame 300 is easily coupled to the supports 200 to be rotatable about a first rotary shaft 900 of which a first end is disposed through the first rotational hole 210 and the second rotational hole 310. The outer frame 300, which is a part rotating with the first rotary shaft 900, can be made of any materials as long as the materials satisfy necessary strength.

The inner frame 400 is formed by four members coupled in a rectangle, disposed inside the outer frame 300, and rotating about an axis perpendicular to the rotational direction of the outer frame 300. A third rotational hole 410 is formed through the members of the inner frame 400 for easy coupling. That is, the inner frame is disposed inside the outer frame 300 to be rotatable about a second rotary shaft 950 of which a first end is disposed through the third rotational hole 410 and the second rotational hole 310. The second rotary shaft 950 and the first rotary shaft 900 are disposed perpendicular to each other, that is, the second rotary shaft 950 is disposed through members perpendicular to the members through which the first rotary shaft 900 is disposed, with respect to the outer frame 300. The inner frame 400, which is a part rotating with the second rotary shaft 950, can be made of any materials as long as the materials satisfy necessary strength.

The cultivating plate 500 is a part fixed inside the inner frame 400 to cultivate cells. The cultivating plate 500 is provided to allow for cultivation of cells in a space environment, that is, under microgravity, using rotation of the outer frame 300 and the inner frame 400. The cultivate plate 500 is a common plate for cultivating cells.

The first motor unit 600 is disposed on the base plate 100 or one of the supports 200 and connected to the outer frame 300 to transmit torque. The first motor unit 600 is one of the configurations controlled by the controller 700 to be described below so that cells are cultivated on the cultivating plate 500 in a microgravity environment. That is, cells on the cultivating plate 500 can be cultivated under a microgravity environment by the first motor unit 600 and the second motor unit 650 to be described below. The first motor unit 600, which is connected to a second end of the first rotary shaft 900 through a first belt 910 to rotate about the first rotary shaft 900, is commonly used in 3D clinostats.

The second motor unit 650 is disposed on one of the outer sides of the outer frame 300 and connected to the inner frame 400 to transmit torque. The second motor unit 650 is one of the configurations controlled by the controller 700 to be described below so that cells are cultivated on the cultivating plate 500 in a microgravity environment. The second motor unit 650, which is connected to a second end of the second rotary shaft 950 through a second belt 960 to rotate about the second rotary shaft 950, is commonly used in 3D clinostats.

According to the present invention, a first rotary gear 920 and a second rotary gear 970 may be disposed at the second ends of the first rotary shaft 900 and the second rotary shaft 950, respectively, in order that torque from the first motor unit 600 and the second motor unit 650 can be easily transmitted. That is, the first rotary gear 920 and the second rotary gear 970 are disposed on the first rotary shaft 900 and the second rotary shaft 950, respectively to make sure that torque from the first motor unit 600 and the second motor unit 650 can be transmitted. The first rotary gear 920 and the second rotary gear 970 are common gears connected to a motor to transmit torque.

The controller 700, as shown in FIG. 7, is electrically connected to the first motor unit 600 and the second motor unit 650 to control the first motor unit 600 and the second motor unit 650. The controller 700 controls rotation of the first motor unit 600 and the second motor unit 650 so that cells on the cultivating plate 500 can be cultivated under microgravity by rotating the inner frame 400 and the outer frame 300. As the controller 700, various common devices may be used, but a computer is used for easy control. A program for controlling the first motor unit 600 and the second motor unit 650 so that cells on the cultivating plate 500 can be cultivated under microgravity is installed in the computer used as the controller 700.

The output unit fixing member 800 is fixed inside the inner frame 400, at a predetermined distance from the top of the cultivating plate 500 and has the longitudinal oblong fixing long 810. One end or both ends of the output unit fixing member 800 are fixed to a side on the top of the inner frame 400. The output unit fixing member 800 may be made of any materials as long as the ultrasonic wave output unit 820 is can be fixed to the top of the inner frame 400.

The ultrasonic wave output unit 820 is a device that is disposed inside the oblong fixing hole 810 of the output unit fixing member 800 and applies an ultrasonic wave stimulus to cells cultivated on the cultivating plate 500. The ultrasonic wave output unit 820 is a conventional device typically used to output ultrasonic wave in the field of ultrasonic wave treatment.

The ultrasonic device 850, as shown in FIG. 3, is a conventional ultrasonic device connected to the ultrasonic wave output unit 820 to stimulate the cells on the cultivating plate 500. The ultrasonic device 850 applies a stimulus to cells with various magnitudes to remove an adverse influence on cells under microgravity. That is, the ultrasonic device 850 removes an adverse influence on cells under microgravity by stimulating the cells with various magnitudes (ultrasonic wave pulse and continuous time of pulse repeat frequency) in accordance with a change in cells under microgravity.

The first rotary shaft 900 and the second rotary shaft 950 used in the present invention are slip rings. As shown in FIG. 3, the controller 700, the first motor unit 600, and the second motor unit 650 may be directly connected, but an electric wire connecting the controller 700, the first motor unit 600, and the second motor unit 650 may be disposed through the slip rings to prevent the electric wire from being entangled even if the frames are rotated. Further, as shown in FIG. 3, the ultrasonic wave output unit 820 and the ultrasonic device 850 may be directly connected, but an electric wire connecting the ultrasonic wave output unit 820 and the ultrasonic device 850 may be disposed through the slip rings to prevent the electric wire from being entangled even if the frames are rotated. Since the first rotary shaft 900 and the second rotary shaft 950 are slip rings in the present invention, wiring for the first motor unit 600, the second motor unit 650, and the ultrasonic wave output unit 820 is not complicated and the electric wires are not entangled even due to rotation of the frames, so the electric wires are not damaged.

Figure 5:
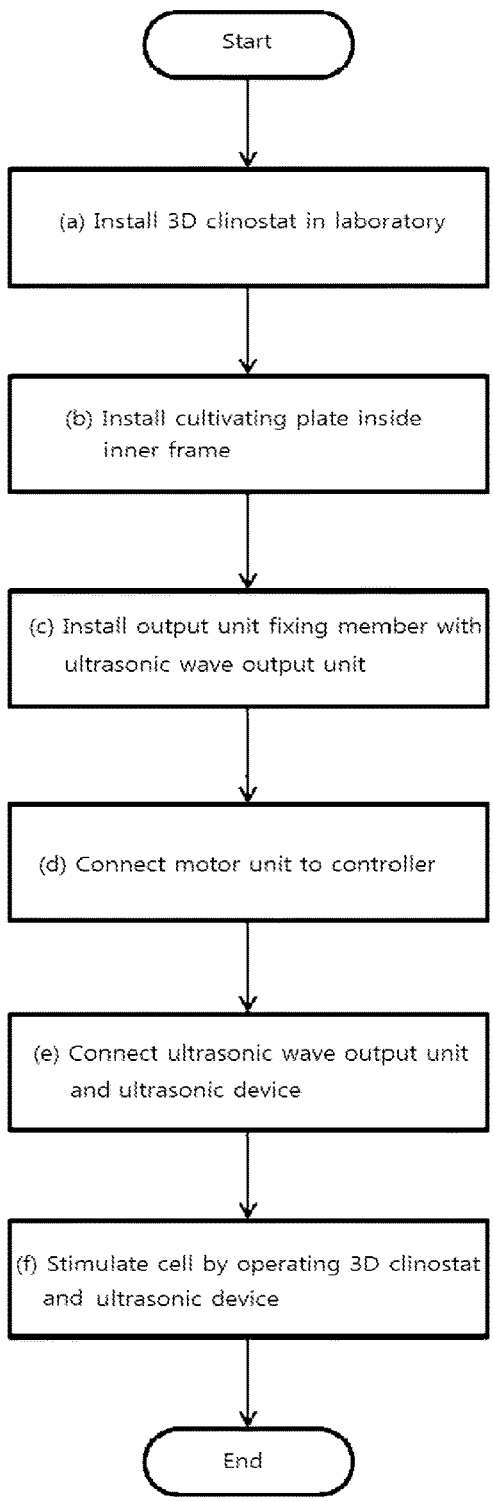
FIG. 5 is a flowchart illustrating a method of stimulating cells of the present invention.

FIG. 5 is a flowchart illustrating a method of stimulating cells of the present invention.

The present invention provides an apparatus 10 for stimulating cells using a 3D clinostat and ultrasonic waves, specifically, in experiment equipment for studying adverse influences on a human body under microgravity and taking a countermeasure against the influences. The method includes: (a) installing a 3D clinostat, which includes: a base plate 100; supports 200 each having a first end coupled to a side on the top of the base plate 100; an outer frame 300 formed by four members coupled in a rectangle and rotating about an axis between the two supports 200 spaced at a predetermined distance from each other; an inner frame 400 formed by four members coupled in a rectangle, disposed inside the outer frame 300, and rotating about an axis perpendicular to the rotational direction of the outer frame 300; a first motor unit 600 disposed on the base plate 100 or one of the supports 200 and connected to the outer frame 300 to transmit torque; a second motor unit 650 disposed on the outer side of the outer frame 300 and connected to the inner frame 400 to transmit torque, into a laboratory; (b) fixing a cultivating plate 500 for cultivating cells inside the inner frame 400; (c) disposing an output unit fixing member 800 having a longitudinal oblong fixing hole 810 with an ultrasonic wave output unit 820 fixed therein, at a predetermined distance from the top of the cultivating plate 500; (d) connecting a controller 700 to the first motor unit 600 and the second motor unit 650; (e) connecting an ultrasonic wave output unit 820 and an ultrasonic device 850; and (f) stimulating cells on the cultivating plate 500 by operating the controller 700 and the ultrasonic device 850.

The present invention relates to a method of stimulating cells using a 3D clinostat that includes steps (a) to (f). That is, the present invention relates to a method of stimulating cells using the apparatus 10 for stimulating cells to study an adverse influence on cells under a space environment, that is, a microgravity environment, and a countermeasure against the adverse influence. The description of the apparatus 10 for stimulating cells is substituted for description of components that will not be described hereafter.

The step (a) is to set an apparatus composed of the base plate 100, the supports 200, the outer frame 300, the inner frame 400, the first motor unit 600, and the second motor unit 650 in a laboratory or at a predetermined space.

The step (b) is to fix the cultivating plate 500 for cultivating cells inside the inner frame 400. The cultivating plate 500 is fixed inside the inner frame 400 in order not to be separated from the inner frame 400 when the inner frame 400 is rotated.

The step (c) is to fix the output unit fixing member 800 with the ultrasonic wave output unit 820 fixed thereto, to the inner frame 400 at a predetermined distance from the top of the cultivating plate 500. The output unit fixing member 800 is fixed to the top of the inner frame 400 in order not to be separated from the inner frame 400 when the inner frame 400 is rotated.

The step (d) is to electrically connect the controller 700 to the first motor unit 600 and the second motor unit 650, in which electric wires are disposed not to be entangled when the frames are rotated.

The step (e) is to connecting the ultrasonic wave output unit 820 and the ultrasonic device 850, in which electric wire is disposed not to be entangled even though the frames are rotated.

The step (f) is to stimulate cells on the cultivating plate 500 by operating the controller 700 and the ultrasonic device 850. The step (f) is to operate the controller 700 and the ultrasonic device 850 in order to study an adverse influence on cells under a microgravity environment and a countermeasure against the adverse influence.

The present invention further includes first rotary holes 210 formed through second ends of the supports 200; second rotary holes 310 formed through the members of the outer frame 300; third rotary holes 410 formed through the members of the inner frame 400; a first rotary shaft 900 of which a first end is disposed through the first rotational holes 210 and the second rotational holes 310; and a second rotary shaft 950 of which a first end is disposed through the second rotational holes 310 and the third rotational holes 410. The first motor unit 600 may be connected to a second end of the first rotary shaft 900 through a first belt 910 so that the outer frame 300 rotates about the first rotary shaft 900 and the second motor 650 may be connected to a second end of the second rotary shaft 950 so that the inner frame 400 rotates about the second rotary shaft 950. According to the present invention, a first rotary gear 920 and a second rotary gear 970 may be disposed at the second ends of the first rotary shaft 900 and the second rotary shaft 950, respectively, in order that torque from the first motor unit 600 and the second motor unit 650 can be easily transmitted.

The components can be added to make coupling among them clear and to easily combine them and were described in detail in relation to the apparatus 10 for stimulating cells in the present invention.

Further, the first rotary shaft 900 and the second rotary shaft 950 are slip rings, so it is possible to prevent the wires disposed through the slip rings from being entangled.

Although exemplary embodiments of an apparatus and a method of stimulating cells using a 3D clinostat and ultrasonic waves were described above, the spirit, the configuration, and the operation of the present invention are not limited thereto and the scope of the present invention is not limited to the drawings or the description referring to the drawings. Further, the concept and embodiments of the present invention described above may be used as the base for changing or designing the present invention into other ways to achieve the same objects by those skilled in the art, but the equivalent modifications and changes by those skilled in the art are included in the scope of the present invention described in claims and the present invention may be changed and modified in various ways without departing from the spirit or scope of the present invention described in claims.

REFERENCE SIGNS LIST

| | |
|---|---|
| 10: Apparatus for stimulating cell | |
| 100: Base plate | 200: Support |
| 210: First rotational hole | 300: Outer frame |
| 310: Second rotational hole | 400: Inner frame |
| 410: Third rotational hole | 500: Cultivating plate |
| 600: First motor unit | 650: Second motor unit |
| 700: Controller | 800: Output unit fixing member |
| 810: Oblong fixing hole | 820: Ultrasonic wave output unit |
| 850: Ultrasonic device | 900: First rotary shaft |
| 910: First belt | 920: First rotary gear |
| 950: Second rotary gear | 960: Second belt |
| 970: Second rotary gear | |

The invention claimed is:

1. An apparatus for stimulating cells using a three dimensional (3D) clinostat and ultrasonic waves in experiment equipment for studying adverse influences on a human body under microgravity and taking a countermeasure against the influences, the apparatus comprising:

a base plate;

supports each having a first end coupled to a side on a top of the base plate;

an outer frame formed by four members coupled in a rectangle and rotating about an axis between the supports spaced at a predetermined distance from each other;

an inner frame formed by four members coupled in a rectangle, disposed inside the outer frame, and rotating about an axis perpendicular to a rotational direction of the outer frame;

a cultivating plate fixed inside the inner frame to cultivate cells;

a first motor unit disposed on the base plate or one of the supports and connected to the outer frame;

a second motor unit disposed on an outer side of the outer frame and connected to the inner frame;

a controller electrically connected to the first motor unit and the second motor unit to control the first motor unit and the second motor unit;

an ultrasonicator fixing member fixed to the inner frame at a predetermined distance from a top of the cultivating plate and having a longitudinally oblong fixing hole; and an ultrasonicator disposed at a side in the oblong fixing hole of the ultrasonicator fixing member and configured to stimulate the cells on the cultivating plate.

2. The apparatus of claim 1, further comprising:

first rotational holes formed through second ends of the supports;

second rotational holes formed through the members of the outer frame;

third rotational holes formed through the members of the inner frame;

a first rotary shaft of which a first end is disposed through the first rotational holes and the second rotational holes; and a second rotary shaft of which a first end is disposed through the second rotational holes and the third rotational holes, wherein the first motor unit is connected to a second end of the first rotary shaft through a first belt so that the outer frame rotates about the first rotary shaft, and the second motor is connected to a second end of the second rotary shaft so that the inner frame rotates about the second rotary shaft.

3. The apparatus of claim 2, wherein the first rotary shaft and the second rotary shaft are slip rings.

4. The apparatus of claim 2, further comprising:
a first rotary gear disposed at the second end of the first rotary shaft; and
a second rotary gear disposed at the second end of the second rotary shaft.

5. A method of stimulating cells using a three dimensional (3D) clinostat and ultrasonic waves to study adverse influences on a human body under microgravity and to take a countermeasure against the influences, the method comprising:

(a) installing the 3D clinostat including:
a base plate;
supports each having a first end coupled to a side on a top of the base plate;
an outer frame formed by four members coupled in a rectangle and rotating about an axis between the supports spaced at a predetermined distance from each other;
an inner frame formed by four members coupled in a rectangle, disposed inside the outer frame, and rotating about an axis perpendicular to a rotational direction of the outer frame;
a first motor unit disposed on the base plate or one of the supports and connected to the outer frame; and
a second motor unit disposed on an outer side of the outer frame and connected to the inner frame;
(b) fixing a cultivating plate for cultivating cells inside the inner frame;

(c) disposing an ultrasonicator fixing member having a longitudinal oblong fixing hole with an ultrasonicator fixed therein, at a predetermined distance from a top of the cultivating plate, wherein the ultrasonicator is configured to stimulate the cells on the cultivating plate;
(d) connecting a controller to the first motor unit and the second motor unit;
and
(e) stimulating the cells on the cultivating plate by operating the controller.

6. The method of claim 5, further comprising:
first rotational holes formed through second ends of the supports;
second rotational holes formed through the members of the outer frame;
third rotational holes formed through the members of the inner frame;
a first rotary shaft of which a first end is disposed through the first rotational holes and the second rotational holes; and
a second rotary shaft of which a first end is disposed through the second rotational holes and the third rotational holes,
wherein the first motor unit is connected to a second end of the first rotary shaft through a first belt so that the outer frame rotates about the first rotary shaft, and
the second motor is connected to a second end of the second rotary shaft so that the inner frame rotates about the second rotary shaft.

7. The method of claim 6, wherein the first rotary shaft and the second rotary shaft are slip rings.

8. The apparatus of claim 6, further comprising:
a first rotary gear disposed at the second end of the first rotary shaft; and
a second rotary gear disposed at the second end of the second rotary shaft.

* * * * *